(12) United States Patent
Seljelid

(10) Patent No.: US 6,423,832 B1
(45) Date of Patent: Jul. 23, 2002

(54) CARBOHYDRATES AND USE THEREOF

(75) Inventor: Rolf Seljelid, Tromsø (NO)

(73) Assignee: Biotec Pharmacon ASA, Tromsö (NO)

(*) Notice: Subject to any disclaimer, the term of this patent is extended or adjusted under 35 U.S.C. 154(b) by 0 days.

(21) Appl. No.: 09/455,464

(22) Filed: Dec. 6, 1999

Related U.S. Application Data

(63) Continuation of application No. PCT/NO98/00170, filed on Jun. 5, 1998.

(30) Foreign Application Priority Data

Jun. 6, 1997 (SE) .............................................. 9702173

(51) Int. Cl.$^7$ .......................... A61K 31/715; C07H 1/00
(52) U.S. Cl. ......................................... 536/1.11; 514/54
(58) Field of Search ............................ 536/1.11; 514/54

(56) References Cited

U.S. PATENT DOCUMENTS 4,795,745 A    1/1989    Larm et al.

FOREIGN PATENT DOCUMENTS

| EP | 0147375 A1 | 7/1985 |
|----|------------|--------|
| EP | 0175667 A2 | 3/1986 |
| JP | 4-214701   | 5/1992 |

*Primary Examiner*—Ralph Gitomer
*Assistant Examiner*—Devesh Khare
(74) *Attorney, Agent, or Firm*—Burns, Doane, Swecker & Mathis, LLP

(57) ABSTRACT

The invention relates to new etherified carbohydrate derivatives, a method for production thereof, pharmaceutical compositions containing the same and use for the production of a pharmaceutical preparation for treatment of conditions in which macrophages are stimulated or down-regulated. In an embodiment of the present invention, said carbohydrate derivatives comprise general formula (I) wherein n is an integer in the range from 3 to 98, and each group R independently represents a hydrogen atom or an aliphatic, saturated or unsaturated hydrocarbon chain having from 7 to 30 carbon atoms.

40 Claims, 5 Drawing Sheets

Release of IL-1 from mouse macrophages (MO) in vivo after treatment for 24 h.

Release of α-TNF from mouse macrophages (MO) after treatment for 8 h.

CARBOHYDRATES AND USE THEREOF

This is a continuation of International Application No. PCT/NO98/00170, filed Jun. 5, 1998, that designates the United States of America and which claims priority from Swedish Application No. 9702173-7, filed June 6, 1997.

FIELD OF THE INVENTION

The present invention relates to carbohydrate derivatives having an immunomodulating effect, pharmaceutical compositions containing the same, and use of the carbohydrate derivatives in the manufacture of a medicament for therapy.

BACKGROUND ART

Immunomodulators, in the following referred to as IMs, are a group of non-endogenous compounds which modulate macrophages and related cell types, thereby stimulating or down-regulating the immune defence of the body. In most cases this modulation consists of a stimulation of macrophages and related cell types.

By the term "macrophages" is meant, inter alia, cells having the capability of enclosing particles having a size of about 1–10 μm and additionally affecting their environment by means of secretion of biologically active substances. The term "macrophages" also comprises related cell types, such as coelomocytes and most phagocytes of lower animals (invertebrates), promonocytes, monocytes, Kupffer cells, microglial cells, histiocytes and tissue macrophages of higher animals (vertebrates) and various types of syncytia cells and giant cells which are formed by fusion with individual macrophages.

A large number of IMs consist of carbohydrates, such as β1→3-glucans and alginates (salts of polymannuronic acid), or contain carbohydrate units, such as bacterial lipopolysaccharides, LPS and peptidoglycans. Some of these compounds, for instance LPS, are toxic and consequently not suitable for use in human or veterinary medicine in those cases where an immunity-enhancing effect is desired. Other IMs, such as β1→3-glucans, seem to be virtually nontoxic although they have a clear biological activity both in vitro and in vivo. As examples of pharmacological effects caused by the latter compounds mention can be made of, inter alia, strong stimulation of the production of cytokine, nitric oxide and arachidonic acid metabolites in macrophages (Seljelid, R. and Eskeland, T., *Eur J. Haematol.*, 51, 267–275, 1993; Seljelid, R. and Busund, L.-T. R., *Eur J. Haematol.*, 52, 1–12, 1994; Sveinbjørnsson, B., Olsen, R., Seternes, O. M. and Seljelid, R., *Biochem. Biophys. Res. Comm.*, 223, 643–649, 1996), resistance to lethal infections in both mammals and lower vertebrates (animals) and invertebrates (Dalmo, R. A., Bøgwald, J., Ingebrigtsen, K. and Seljelid, R., *J Fish Diseases*, 19, 449–457, 1996; Busund, L-T., Rasmussen and Seljelid, R., in *Molecular Pathogenesis of Surgical Infections*, Wadstr öm. T., Holder, I. A., Kronvall, G. (eds.), *Proceedings of the Eric K. Fernström Symposium*, Lund, pp 293–302, 1992), regression of syngeneic tumours in mice (Seljelid, R., *Bioscience Reports*, 6, 845–851, 1986; Seljelid, R., *Scand. J. Immunol.*, 29, 181–192, 1989) and prevention of metastases in experimental tumours in rats (Sveinbjørnsson et al, in press).

In those cases where carbohydrate immunomodulators, below referred to as CIMs, have been hydrolysed in connection with the production of oligosaccharides, the biological activity in general has disappeared (Seljelid, R., Bøgwald, J. and Lundwall, Å., *Exp. Cell. Res.*, 131, 121–129, 1981; Seljelid, R. et al, *Scand. J. Immunol.*, in press, 1997).

It is also known to modify existing CIMs while maintaining their biological activity in respect of stimulation of macrophages in vitro. Such a modification is the substitution of a hydroxyl group with an amino group (Bøgwald, J., Seljelid, R. and Hoffman. J., *J. Carbohydr. Res.*, 148, 101–107, 1986; Rasmussen, L.-T. and Seljelid, R., *Scand. J. Immunol.*, 32, 321–331, 1990), the resulting aminated β1→3-glucan besides being found to be water-soluble contrary to the non-modified β1→3-glucan. This may be caused by the fact that precisely the hydroxyl groups which are important to the aggregate formation in β1→3-glucan (vide infra), which aggregate formation lowers its solubility, have been substituted by amino groups which complicate the aggregate formation, resulting in the net effect that the solubility increases significantly in said amino substitution.

U.S. Pat. No. 4,795,745 A discloses a composition in which soluble β1→3-glucan has been bound to a water-insoluble carrier, which results in a composition which accomplishes activation of macrophages.

Another type of modified β1→3-glucan is disclosed in JP 04-2140701 A, in which the hydroxyl groups of a β1→3-glucan having a molecular weight from 200 and 800 g/mole have been etherified with both lower hydroxyalkyl groups having 2–4 carbon atoms and higher alkyl groups having 8–26 carbon atoms. These compounds are used for e.g. cosmetic and medicinal purposes.

General Description of the Invention

A common denominator of the carbohydrates, and especially β1→3-glucans, which are known up to now as immunomodulating substances is that their binding to receptors on the cell surfaces of macrophages and related cell types mainly occurs via hydrogen bonds. This is obvious when observing that the most important functional groups in addition to the actual carbon skeleton are either hydroxyl or amino groups, below referred to as hydrogen-binding groups, which both have the capacity of binding to, for instance, a receptor by means of hydrogen bonds. If one or more of these hydrogen-binding groups are replaced with non-hydrogen-binding groups, the binding of the compounds to the receptor or receptors will therefore probably be weakened since the substrate, i.e. the carbohydrate, loses one or more binding positions. The weakening will probably be greater, the lower hydrogen-binding capacity the substituting group presents. Moreover, steric hindrances, if any, are often important to the binding, and since both hydroxyl and amino groups from a sterical point of view are relatively unhindered groups, a sterically hindered substituent for one of these groups may weaken the binding to the receptor or receptors. As a rule, the weakening of the binding increases, the more sterically hindered the substituent is.

Summing up the above discussion, it may therefore be established that a substituent to hydroxyl or amino groups which has both a lower hydrogen-binding capacity and a larger sterical hindrance than any one of the above-mentioned groups is in the first place expected to cause a weakening of the binding of a carbohydrate to a receptor.

However, according to the present invention it has surprisingly been found that immunomodulating carbohydrates which have been etherified with aliphatic hydrocarbon chains have an immunomodulating effect and, thus, stimulate machrophages and related cell types. For these etherified immunomodulating carbohydrates, the expected weakening of the receptor binding to the macrophages has thus not occurred.

The IMs which consist of pure carbohydrates, such as β1→3-glucans, alginates and agarose, are of course hydrophilic, but are all the same poorly soluble in water owing to their high molecular weight in combination with aggregate formation and intermolecular hydrogen bonds. Since these properties often reduce the general bioavailability of the compounds, this is disadvantageous for their use as pharmaceutical preparations, above all in respect of, inter alia, dosage, uptake, distribution and biological half-life in the body after administration. It is known (vide supra) that modified β1→3-glucans are often more easily water-soluble than the non-modified starting material in spite of a seemingly insignificant modification of the said type of compound. It thus seems probable that also minor changes are in many cases sufficient to considerably affect, for instance, intermolecular hydrogen bonds and aggregate formation, which to a high extent cause the insignificant water solubility of many non-modified IMs.

The etherification of the compounds according to the present invention supplies an improvement of the lipophilic properties of the compounds. These new lipophilic properties affect, inter alia, dosage, uptake, distribution and biological half-life in the body after administration in a favourable manner with maintained or improved biological activity. The increased lipophilicity of the compounds according to the present invention results in their general capacity of penetrating skin being good, whereby topical administering forms are particularly advantageous owing to the improved receptivity.

An aim of the invention thus is to present a completely new class of compounds comprising etherified carbohydrates having an immunomodulating effect.

One more aim of the present invention is to provide new carbohydrate derivatives which have been etherified with one or more aliphatic hydrocarbon chains, said carbohydrate derivatives stimulating macrophages and related cell types.

A further aim of the present invention is to provide etherified carbohydrate derivatives which have more favourable preparation and administration properties than the corresponding non-etherified carbohydrates.

A still further aim of the present invention is to provide etherified carbohydrate derivatives, whose aliphatic hydrocarbon chains can be modified by further substitution or unsaturation, thereby affecting, for instance, dosage, uptake, distribution and biological half-life in a favourable manner.

Another aim of the present invention is to provide etherified carbohydrate derivatives for use as pharmaceutical preparations.

One more aim of the present invention is to provide a pharmaceutical composition comprising carbohydrate derivatives which have been etherified with one or more aliphatic hydrocarbon chains.

A further aim of the present invention is to provide use of etherified carbohydrate derivatives for the preparation of a medicament for treatment of conditions in which macrophages and related cell types are of importance.

Another aim of the present invention is to provide a method of preparing etherified carbohydrate derivatives having an immunomodulating effect.

DETAILED DESCRIPTION OF THE INVENTION

The present invention provides new carbohydrate derivatives having an immunomodulating effect. By immunomodulating effect is understood that the new carbohydrate derivatives stimulate or down-regulate macrophages and related cell types and are usable for treatment of inflammatory, infectious or degenerative conditions.

The new carbohydrate derivatives according to the present invention have an immunomodulating effect and contain an oligo- or polysaccharide, said oligo- or polysaccharide comprising at least 5 monosaccharide units in the carbohydrate chain, preferably from 5 to 100 monosaccharide units, more preferred from 5 to 60 monosaccharide units, still more preferred from 5 to 20 monosaccharide units, even more preferred from 5 to 10 monosaccharide units, most preferred from 5 to 8 monosaccharide units, and very most preferred 6 or 7 monosaccharide units. In these carbohydrate derivatives, one or more of the hydroxyl groups are etherified with one or more identical or different aliphatic hydrocarbon chains containing at least 7 carbon atoms, preferably from 7 to 30 carbon atoms, more preferred from 12 to 22 carbon atoms, still more preferred from 16 to 20 carbon atoms, and most preferred 18 carbon atoms. The degree of etherification of these carbohydrate derivatives is about 10–90% by weight, preferably about 30–70% by weight, more preferred about 40–60%, by weight, and most preferred about 50%. The most preferred degree of etherification can also be expressed as the amount of etherified hydroxyl groups, about 50% by weight corresponding to the condition that about ⅔ of the hydroxyl groups are etherified with aliphatic hydrocarbon chains. Moreover, these aliphatic hydrocarbon chains can optionally be further substituted with preferably one or more halogen atoms and/or protected or unprotected hydroxyl groups The etherified carbohydrate derivatives of the invention are preferably derivatives or analogues of β1→3-glucan, curdlan, alginic acid, agarose, laminaran, yeast glucan or another glucan.

A preferred embodiment of the present invention comprises an etherified carbohydrate derivative having the following general formula I:

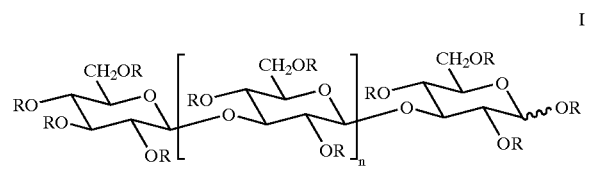

wherein n is an integer in the range from 3 to 98, preferably an integer from 3 to 58, more preferred an integer from 3 to 15, still more preferred an integer from 3 to 15, even more preferred an integer from 3 to 12, yet even more preferred an integer from 3 to 10, particularly more preferred an integer from 3 to 8, even more particularly preferred an integer from 3 to 6, and most preferred n=4 or 5; and each group R independently represents a hydrogen atom or an aliphatic hydrocarbon chain containing from 7 to 30 carbon atoms, more preferred from 12 to 22 carbon atoms, still more preferred from 16 to 20 carbon atoms, and most preferred 18 carbon atoms, said hydrocarbon chain being either saturated or unsaturated. It will be appreciated that the aliphatic hydrocarbon chain may be straight or branched. In the very most preferred embodiment, R is an n-octadecanyl group.

Besides, within the scope of the invention R can optionally be additionally substituted with preferably one or more halogen atoms and/or protected or unprotected hydroxyl groups. The degree of etherification of the preferred carbohydrate derivative according to formula I above is about 10–90% by weight, preferably about 30–70% by weight, more preferred about 40–60% by weight, and most preferred about 50%. The most preferred degree of etherification of the carbohydrate derivative according to formula I can also be expressed as the amount of etherified hydroxyl groups, about 50% by weight corresponding to the condition that about ⅔ of the hydroxyl groups are etherified with aliphatic hydrocarbon chains.

According to the present invention there is also provided an etherified carbohydrate derivative according to the invention for use as a pharmaceutical. Thus, it may be used in pharmaceutical compositions for oral, intravenous, topical, intraperitoneal or subcutaneous administration, in association with one or more pharmaceutically acceptable carriers, diluents or adjuvants that are well known in the art.

The pharmaceutical composition of the invention may be administered topically, in the form of solutions, suspensions or systemically, e.g. by oral administration in the form of tablets, capsules, syrups, powders or granules or by parenteral administration in the form of solutions or suspensions, or by subcutaneous administration or by rectal administration in the form of suppositories or transdermally.

The amount of etherified carbohydrate derivatives per dosage unit in the pharmaceutical composition according to the present invention is within the range of from about 1 to 5,000 mg, preferably from about 10 to 1,000 mg, more preferred from about 50 to 500 mg, and most preferred from about 100 to 250 mg. A preferred pharmaceutical composition of the etherified carbohydrate derivatives according to the present invention is specifically designed for topical administration.

Besides, the present invention provides use of the etherified carbohydrate derivatives according to the invention for the manufacture of a medicament for therapeutic or prophylactic treatment. The produced medicament is particularly, although not exclusively, intended for treatment of various inflammatory and degenerative conditions.

The present invention also provides a method for medicinal treatment of immunological disorders in a human or animal patient in which macrophages and related cell types are stimulated or down-regulated, wherein a therapeutically effective amount of a carbohydrate derivative according to the invention is administered to the patient. The method for treatment particularly, although not exclusively, relates to an immunological disorder which manifests itself as an inflammatory or degenerative condition.

The present invention also provides a method for producing the new carbohydrate derivative according to the invention, comprising the step of reacting the oligo- or polysaccharide with an etherifying reagent, for example reacting the oligo- or polysaccharide with an electrophilic reagent containing an aliphatic hydrocarbon chain in a strongly basic solution in a polar solvent, preferably a polar aprotic solvent, in an inert atmosphere. In an embodiment, the oligo- or polysaccharide is curdlan, i. e. β1→3-D-polyglucopyranose, and in a preferred embodiment, the oligo- or polysaccharide is β1→3-D-hexaglucopyranose. According to a further embodiment, the solvent is dry dimethyl sulphoxide and the electrophilic aliphatic hydrocarbon chain is an alkyl iodide, preferably iodooctadecane. The reaction is preferably carried out in a nitrogen gas atmosphere at about 20–60° C. for about 4–120 h. According to a preferred embodiment, the reaction is carried out at about 40° C. for about 24–120 h.

The following non-limiting Examples illustrate the invention in more detail.

EXPERIMENTAL PART

Example 1

Figure 1:
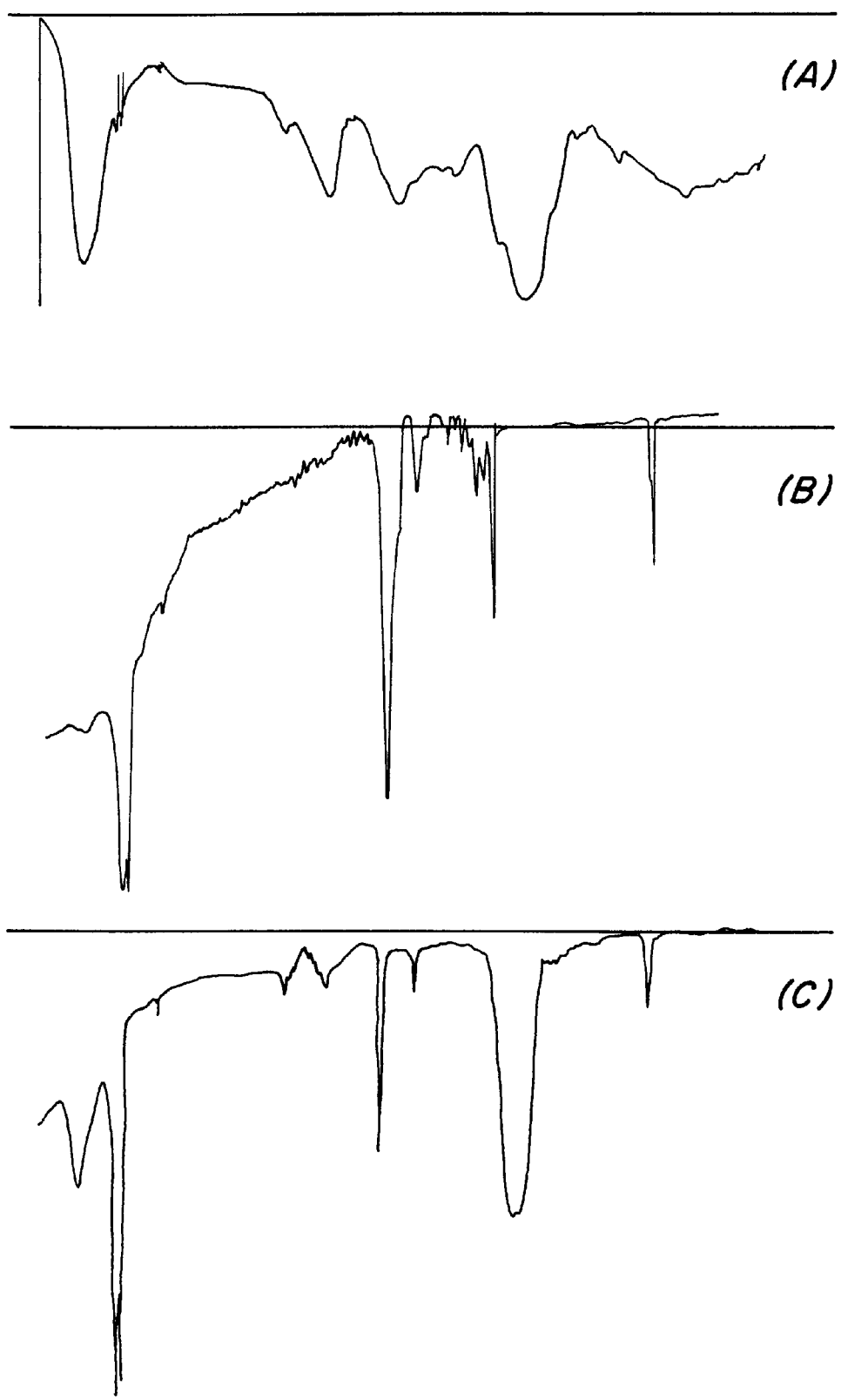
FIG. 1 shows an IR spectrum of curdlan (A), iodooctadecane (B) and hydrolysed curdlan etherified with iodooctadecane (C). All spectra were registered in KBr tablets.

Below follows a description of a general and nonlimiting method for preparation of etherified carbohydrate derivatives of β1→3-glucan which has been obtained from e.g. laminaran, curdlan or yeast glucan. The etherifying reaction is based on deprotonation of a carbohydrate in a dipolar aprotic solvent, such as dimethyl sulphoxide (DMSO), in the presence of pulverulent sodium hydroxide, thereby forming a carbohydrate oxyanion which in turn is etherified by means of an alkyl iodide (Ciucanu, I. and Kerek, F., *Carbodhydr. Res.*, 131, 209–217, 1984).

Production of pulverulent sodium hydroxide:

Dried dimethyl sulphoxide, below referred to as DMSO, is produced by adding 4 Å molecular sieves (4–8 mesh, Fluka. Co., Buchs, Switzerland) to DMSO, whereupon the mixture is stirred at low speed for 3 days. Then 40 ml of the dried DMSO is added to 1 ml of an aqueous solution of sodium hydroxide having a concentration of 1 g/nm. The mixture is then stirred by means of ultrasonication for 4 min in a water bath having a temperature of 30° C. (step A) and is then centrifuged in a table-top centrifuge at 3,000 rpm for 15 min at room temperature (step B). The supernatant is removed (step C) and further 40 ml of dried DMSO is added (step D), whereupon steps A–D as above are repeated 5 times. Finally, the dried pulverulent sodium hydroxide is diluted in dried DMSO to a concentration of 1 g/10 ml.

Production of a β1→3-glucan solution in DMSO:

First the β1→3-glucan is dried overnight in vacuum at room temperature. The dried β1→3-glucan is then mixed with dried DMSO to a concentration of 1 g/25 ml, whereupon the mixture is shaken at 40° C. for 3–5 days.

Etherification of β1→3-glucan with iodooctadecane:

50 ml of a suspension or solution of β1→3-glucan in DMSO of the concentration 1 g/25 ml are mixed with 25 ml of a suspension of pulverulent sodium hydroxide in DMSO of the concentration 1 g/10 ml and 25 ml dried DMSO in a 250 ml round bottom flask. Then the flask is filled with nitrogen gas and sealed, whereupon the mixture is stirred at 40° C. for 24 h. Seven grammes of iodooctadecane (Fluka) are added, whereupon the flask it again filled with nitrogen gas and sealed. After additional stirring at 40° C. for 24 h, the round bottom flask is cooled slowly to room temperature under continuous stirring.

Purification of the product:

The reaction mixture is centrifuged at 3000 rpm for 15 min at room temperature, whereupon the lower liquid phase is removed. The solid phase is again suspended in 150 ml of methanol and stirred for 1 h at room temperature (step A). Subsequently, the suspension is centrifuged at 3,000 rpm for 15 min at room temperature (step B), and the liquid phase is removed (step C). Steps A–C are repeated 3 times, whereupon the dried residue is washed three times with absolute ethanol in the same manner as in steps A–C. Then the residue is dried under a flow of nitrogen gas and then further drying takes place in a desiccator in vacuum for 2–3 days.

The resulting yield usually amounted to 100% in respect of the amount of consumed carbohydrate. The conjugate between hydrolysed curdlan and iodooctadecane, below referred to is C-C18, is a light yellow powder which is soluble in vegetable oils, such as sesame oil, but has low solubility in chloroform ($CHCl_3$). Moreover, K-C18 is easily dispersed in ethanol or acetone. The. structure of K-C18 is represented by the general formula I (p. 7).

Purified K-C18 was analysed by means of HPLC using an analytic reversed phase C-18 column (Millipore, Milford, Mass., USA) at a wavelength of 280 nm. The used mobile phases were either methanol/$CHCl_3$ 20:80, $CHCl_3$ or petroleum/$CHCl_3$ 20:80 and the retention time of K-C18 was in all cases different from the retention time of iodooctadecane and octadecanol, the latter being a by-product in the reaction (Table I). This analysis demonstrated that purified K-C18 was free from contaminations of iodooctadecane and octadecanol.

Figure 2:
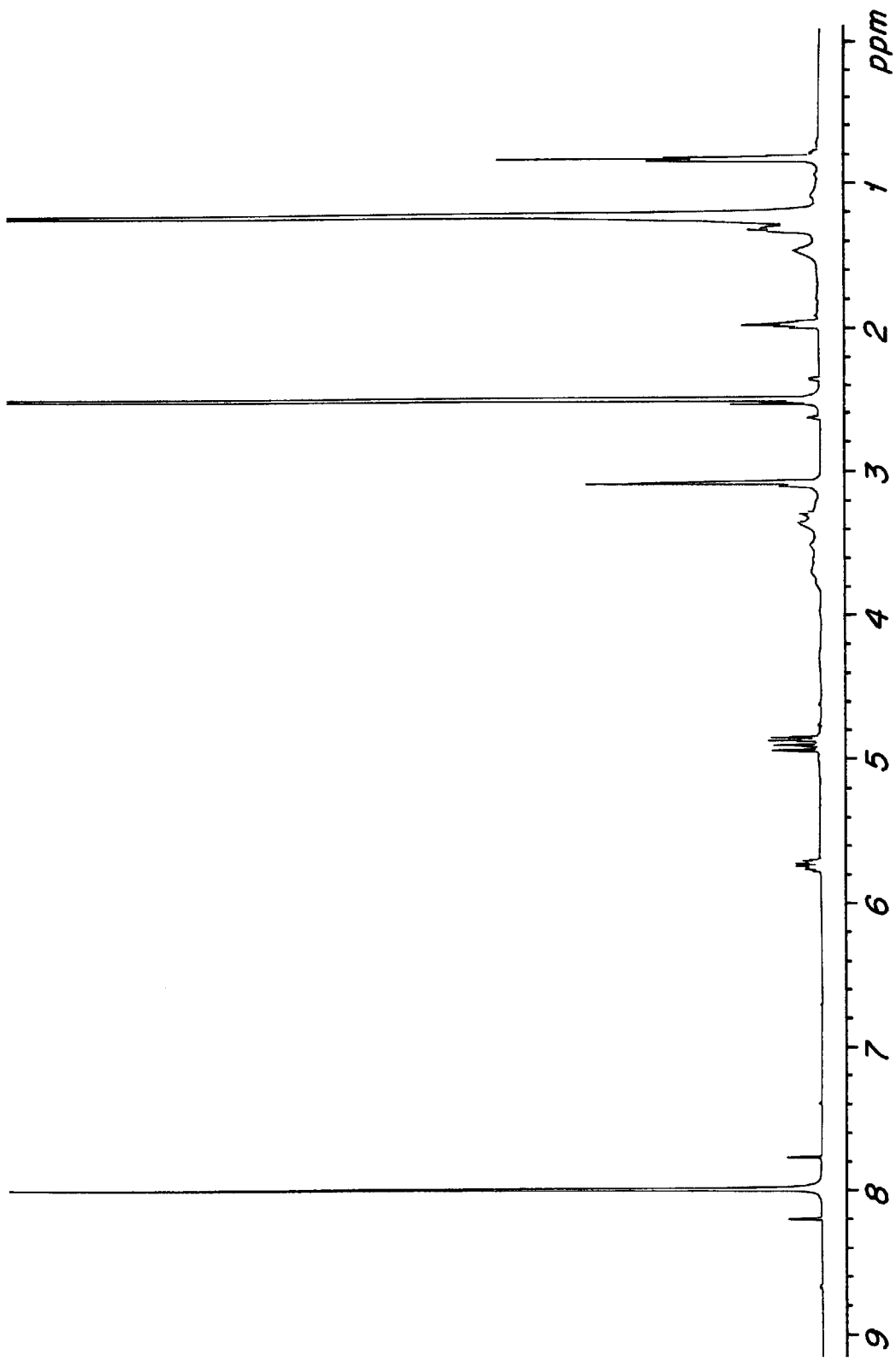
FIG. 2 shows a $^1$H-NMR spectrum (DMSO-$d_6$/CDCl$_3$ 1:1) of hydrolysed curdlan etherified with iodooctadecane. The spectrum was registered at a frequency of 500 MHz at 50° C. for one hour.

IR spectra of curdlan (A), octadecanol (B) and K-C18 (C) are shown in FIG. 1. These spectra clearly show that hydroxyl groups of curdlan have been etherified. In FIG. 2, $^1$H-NMR spectrum in the range of δ 4,92–5.85 show the anomeric protons and the protons of the carbon skeleton of the saccharide units; the methylene protons of the carbohydrate skeleton which are adjacent to the oxygen atom (—O—$CH_2$—) of the ether bond at δ 3.37–3.41; the corresponding methylene protons ($CH_2$—$CH_2$—O—) of the alkyl skeleton at δ 1.25 and the methyl protons at δ 0.88. Owing to the poor solubility of K-C18 in $CHCl_3$, it was not possible to effect a $^{13}$C-NMR analysis of K-C18.

An elementary analysis showed that K-C18 consisted of 65.04% C, 10.30% H and 24.66% O. With the aid of the ratio of C, H and O that was obtained in the elementary analysis, it is possible to determine that on average three monosaccharide units were bound to two C18 alkyl groups. Expressed in % by weight, K-C18 contained 51% C18 alkyl groups and 49% saccharide units. In most cases, 6-O alkylation probably took place, but also 2- and 4-O alkylation could occur.

The same method, optionally with minor changes, can successively be carried out with a large number of other β1→3-glucans, such as laminaran (supplied by US Biochemical Co., Cleveland, Ohio, USA), yeast glucan (prepared by Department of Experimental Pathology, University of Tromsø), alginic acids, agaroses and other oligo or polysaccharides containing a β1→3-glucan unit.

The same method can also be generally used for etherification by means of a reagent containing saturated or unsaturated electrophilic aliphatic hydrocarbon chains having at least 7 carbon atoms, said hydrocarbon chains optionally being further substituted with one or more halogen atoms and/or protected or unprotected hydroxyl groups. The aliphatic hydrocarbon chain affects the lipophilic properties of the carbohydrate derivative and is thus important for, inter alia, the reception, organ distribution and general capacity of the carbohydrate derivative of penetrating skin and other tissue.

Example 2

Below follows a description of a general and nonlimiting method for acid hydrolytic production of oligo- or polysaccharides which are suitable for etherification by means of aliphatic hydrocarbon chains.

10 g curdlan (supplied by Wako Pure Chemical Industries Ltd., Osaka, Japan) is suspended in 500 ml 90% formic acid in a three-necked round bottom flask provided with a reflux cooler and a thermometer, whereupon the mixture is vigorously stirred until all curdlan is dissolved. The flask is placed in a water bath and the curdlan is hydrolysed for about 20–25 min at about 90° C. Then the flask is removed from the water bath and cooled to room temperature. The hydrolysate is evaporated to dryness in vacuum, whereupon 300 ml distilled water are added and the solution is made to boil for 2 h. Subsequently, the hydrolysate is evaporated once more for complete removal of the formic acid, whereupon the hydrolysate is dialysed against distilled water for 3 days with 5 changes of water. The content of the dialysis tube is centrifuged at 3,500 rpm for 20 min and the supernatant is freeze-dried.

Example 3

The determination in vivo of the biological activity of the carbohydrate derivatives according to the present invention is stated below.

Immunomodulating experiments in mice:

0.5 mg K-C18 was dissolved in sesame oil and suspended by means of shaking in 1 ml PBS. 0.1 ml of this suspension was injected into the peritoneal cavity in mice. After 12, 24, 48 and 72 h, peritoneal macrophages were harvested by means of lavage from groups of 5 animals each. The control consisted of macrophages from animals to whom a similar amount of sesame oil had been administered. Then the macrophages were cultivated in vitro under serum-free conditions, and the amount of α-TNF and IL-1 in the medium was analysed by means of known ELISA technique (FIG. 3).

Figure 3:
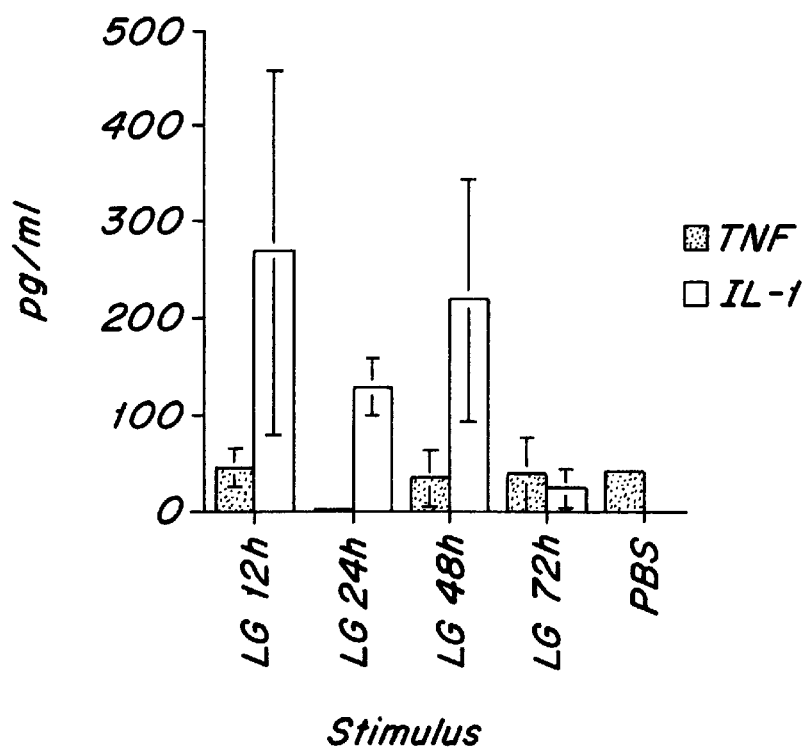
FIG. 3 shows the release of interleukin 1β (IL-1) and tumour necrosis factor a (α-TNF) from mouse macrophages (Mφ) extracted from mice which have been treated with 50 μg of etherified β1→3-glucan (LG) for 12, 24, 48 and 72 h. PBS is the release from macrophages of animals which have been treated with a phosphate-buffered salt solution for 24 h before the cell extraction.

As appears from FIG. 3, K-C18 essentially stimulated the release of IL-1 after 12, 24, and 48 h. After 72 h, the effect seemed to cease. It is also apparent from FIG. 3 that the experimental animals that were treated with K-C18 presented low secretion of α-TNF from macrophages.

Example 4

Figure 4:
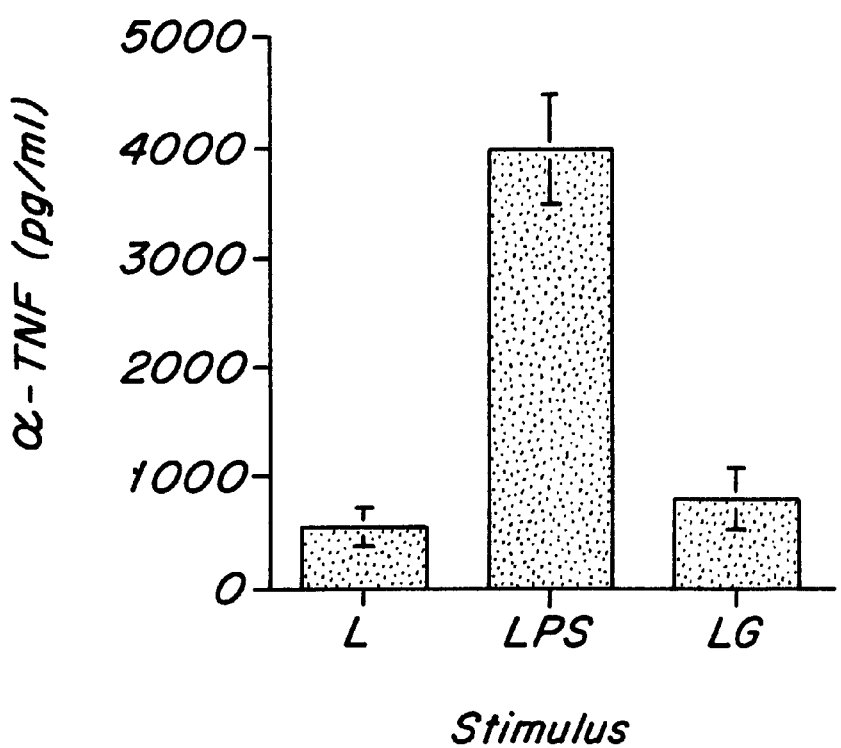
FIG. 4 shows the release of IL-1 from mouse macrophages which have been treated in vitro with etherified β1→3-glucan (LG, 50 μg/ml), bacterial lipopolysaccharide (LPS, 1 μg/ml) or emulsified sesame oil (L, 50 μg/ml) after 24-h-treatment.

Immunomodulating experiments in vitro:

Macrophages from normal non-treated animals were incubated with the etherified β1→3-glucan K-C18 (LG) at a concentration of 50 μg/ml for 24 h, whereby a considerable secretion of IL-1 was observed (FIG. 4). Positive and negative controls were obtained by means of incubation with LPS (1 μg/ml) and sesame oil (L, 50 μg/ml), respectively.

Example 5

Figure 5:
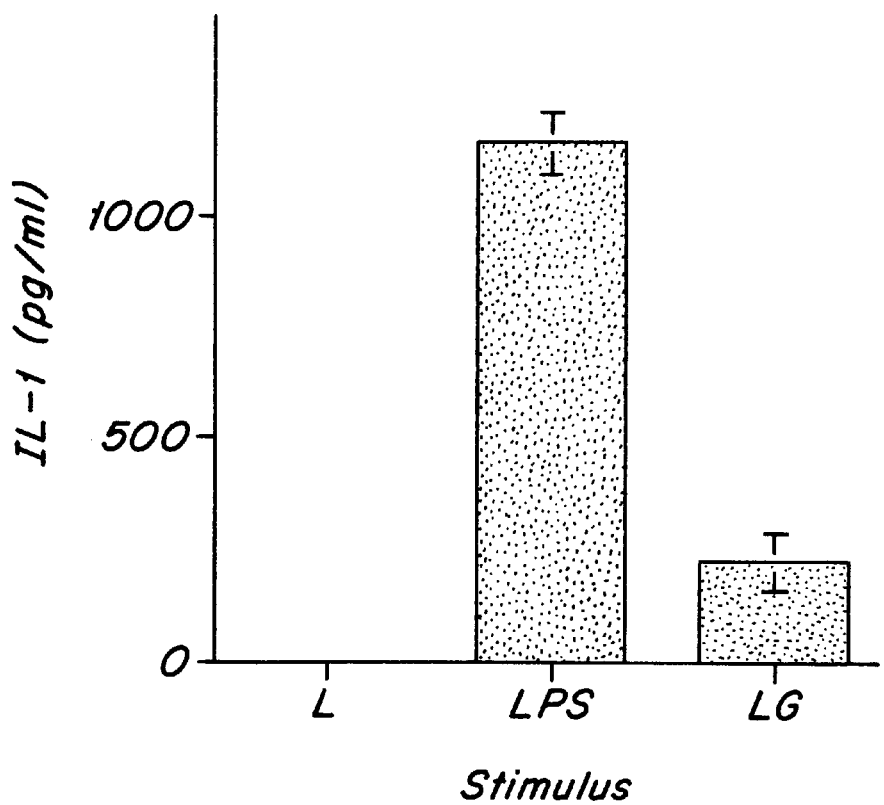
FIG. 5 shows the release of α-TNF from mouse macrophages in vitro after 8-h-treatment. The letters are the same as in FIG. 4.

An analysis of α-TNF under incubation conditions according to Example 4 for 8 h did not demonstrate essentially higher secretion than that obtained in the negative control with sesame oil (FIG. 5).

DISCUSSION

As appears from the present experimental data, the new carbohydrate derivatives according to the present invention stimulate macrophages in vivo as well as in vitro. It is anticipated that said carbohydrate derivatives will have a wide range of application as immunity-enhancing agent in preferably topical and oral administrations. Particularly interesting applications are pharmaceutical preparations intended for treatment of inflammatory, infectious or degenerative conditions.

TABLE 1

Retention times (min) for K-C18, iodooctadecane and ocatadecanol in HPLC analysis

| Eluate | K-C18 | Iodooctadecane | Octadecanol |
|---|---|---|---|
| Methanol/CHCl$_3$ 20:80 | 3.02 | 3.30 | 3.68 |
| CHCl$_3$ | 2.75 | 3.12 | 3.42 |
| Petroleum/CHCl$_3$ 20:80 | 2.83 | 3.07 | 2.35 |

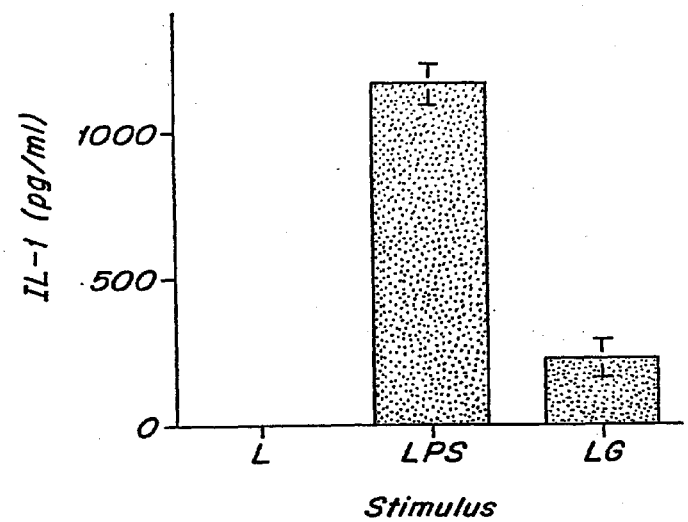

What is claimed is:

1. A carbohydrate derivative having an immunomodulating effect comprising an oligo- or polysaccharide carbohydrate chain, wherein said oligo- or polysaccharide carbohydrate chain is characterized by the general formula I:

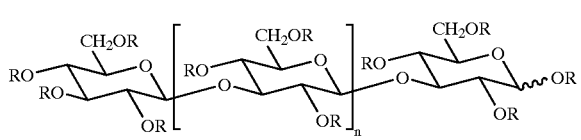

wherein n is an integer in the range from 3 to 98, and

R independently represents a hydrogen atom or an aliphatic, saturated or unsaturated hydrocarbon chain having from 7 to 30 carbon atoms.

2. The carbohydrate derivative of claim 1, wherein said hydrocarbon chain is optionally further substituted with one or more substituents selected from halogen atoms or hydroxyl groups.

3. The carbohydrate derivative of claim 1, wherein said hydrocarbon chain contains from 12 to 22 carbon atoms.

4. The carbohydrate derivative of claim 3, wherein said hydrocarbon chain contains from 16 to 20 carbon atoms.

5. The carbohydrate derivative of claim 4, wherein said hydrocarbon chain contains 18 carbon atoms.

6. The carbohydrate derivative of claim 1, wherein said hydrocarbon chain is an n-octadecanyl group.

7. The carbohydrate derivative of claim 1, wherein n is integer from 3 to 58.

8. The carbohydrate derivative of claim 7, wherein n is integer from 3 to 18.

9. The carbohydrate derivative of claim 8, wherein n is integer from 3 to 15.

10. The carbohydrate derivative of claim 9, wherein n is integer from 3 to 12.

11. The carbohydrate derivative of claim 10, wherein n is integer from 3 to 10.

12. The carbohydrate derivative of claim 7, wherein n is integer from 3 to 8.

13. The carbohydrate derivative of claim 7, wherein n is integer from 3 to 6.

14. The carbohydrate derivative of claim 7, wherein n is integer from 4 to 5.

15. The carbohydrate derivative of claim 1, wherein said carbohydrate derivative is 6-O-aklyated.

16. The carbohydrate derivative of claim 1, wherein said carbohydrate derivative is 6-O- and 2-O-alkylated.

17. The carbohydrate derivative of claim 1, wherein said carbohydrate derivative is 6-O-, 2-O- and 4-O-alkylated.

18. The carbohydrate derivative of claim 1, wherein said aliphatic hydrocarbon chains constitute about 10–90% by weight of the molecular weight of the carbohydrate derivative.

19. The carbohydrate derivative of claim 18, wherein said aliphatic hydrocarbon chains constitute about 30–70% by weight of the molecular weight of the carbohydrate derivative.

20. The carbohydrate derivative of claim 19, herein said aliphatic hydrocarbon chains constitute about 40–60% by weight of the molecular weight of the carbohydrate derivative.

21. The carbohydrate derivative of claim 20, wherein said aliphatic hydrocarbon chains constitute about 50% by weight of the molecular weight of the carbohydrate derivative.

22. The carbohydrate derivative of claim 1, wherein said carbohydrate chain comprises from 5 to 100 monosaccharide units.

23. The carbohydrate derivative of claim 1, wherein said carbohydrate chain comprises a derivative or an analogue of α1→3-glucan, alginic acid, agarose, curdlan, laminaran, yeast glucan or some other glucan.

24. A pharmaceutical composition comprising a carbohydrate derivative of claim 1 in association with a pharmaceutically acceptable adjuvant, diluent or carrier.

25. The pharmaceutical composition of claim 24, wherein the amount of carbohydrate derivative per dosage unit is within the range of about 1 to about 5,000 mg.

26. The pharmaceutical composition of claim 25, wherein the amount of carbohydrate derivative per dosage unit is within the range of about 10 and about 1,000 mg.

27. The pharmaceutical composition of claim 26, wherein the amount of carbohydrate derivative per dosage unit is within the range of about 50 to about 500 mg.

28. The pharmaceutical composition of claim 27, wherein the amount of carbohydrate derivative per dosage unit is within the range of about 100 to about 250 mg.

29. The pharmaceutical composition of claim 24, wherein said composition is for topical administration.

30. A method for the therapeutic or prophylactic treatment of immunological disorders in a human or animal patient comprising administering an effective amount of the carbohydrate derivative of claim 1.

31. A method for the therapeutic or prophylactic treatment of degenerative disorders in a human or animal patient comprising administering an effective amount of the carbohydrate derivative of claim 1.

32. A method for the therapeutic or prophylactic treatment of inflammatory conditions in a human or animal patient comprising administering an effective amount of the carbohydrate derivative of claim 1.

33. A method of treating immunological disorders in a human or animal patient in which macrophages and related cell types are stimulated or down-regulated which comprises administering to the patient a therapeutically effective amount of a carbohydrate derivative of claim 1.

34. The method of treating immunological disorders in a human or animal of claim 33, wherein said immunological disorder manifests itself as an inflammatory or degenerative condition.

35. A method for preparing a carbohydrate derivative of claim 1, comprising the step of reacting the oligo- or polysaccharide with an etherifying reagent.

36. The method of claim 35, wherein said etherifying reagent contains an electrophilic aliphatic hydrocarbon chain.

37. The method of claim 36, wherein said electrophilic aliphatic hydrocarbon chain is an alkyl iodide.

38. The method of claim 36, wherein said electrophilic aliphatic hydrocarbon chain is iodooctadecane.

39. The method of claim 35, wherein said oligo- or polysaccharide is β1→3-D-polyglucopyranose.

40. The method of claim 35, wherein said oligo- or polysaccharide is β1→3-hexaglucopyranose.

* * * * *

UNITED STATES PATENT AND TRADEMARK OFFICE
CERTIFICATE OF CORRECTION

PATENT NO.      : 6,423,832 B1
DATED           : July 23, 2002
INVENTOR(S)     : Rolf Seljelid It is certified that error appears in the above-identified patent and that said Letters Patent is hereby corrected as shown below:

Drawings,
Sheets, consisting of Figs. 3-5, should be deleted to be replaced with the drawing sheets, consisting of Figs. 3-5, as shown on the attached page.

Signed and Sealed this

Third Day of December, 2002

JAMES E. ROGAN
*Director of the United States Patent and Trademark Office*

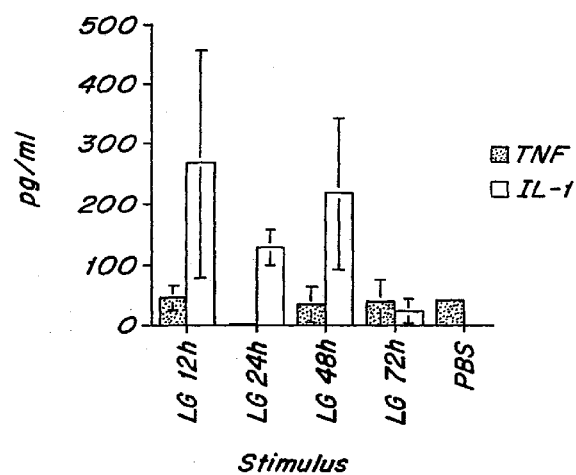

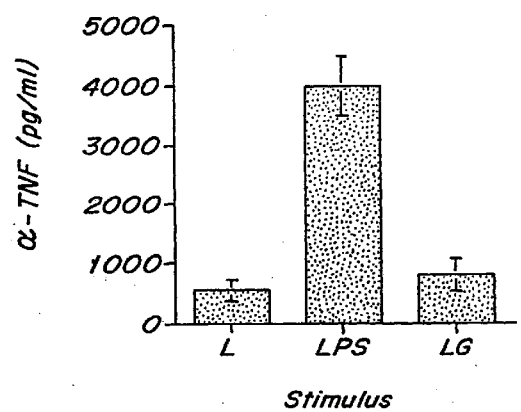
Release of α-TNF from mouse macrophages (MØ) after treatment for 8 h.